United States Patent
Souza et al.

(10) Patent No.: US 9,062,020 B2
(45) Date of Patent: Jun. 23, 2015

(54) 2-((2S,3S,4R,5R)-5-((S)-3-AMINO-2-HYDROXYPROP-1-YL)-4-METHOXY-3-(PHENYLSULFONYLMETHYL)TETRAHYDROFURAN-2-YL) ACETALDEHYDE DERIVATIVES AND PROCESS FOR THEIR PREPARATION

(71) Applicant: ALPHORA RESEARCH INC., Mississauga (CA)

(72) Inventors: Fabio E. S. Souza, Mississauga (CA); Alena Rudolph, Puslinch (CA); Ming Pan, Mississauga (CA); Boris Gorin, Oakville (CA); Dino Alberico, Mississauga (CA)

(73) Assignee: ALPHORA RESEARCH INC., Ontario (CA)

( * ) Notice: Subject to any disclaimer, the term of this patent is extended or adjusted under 35 U.S.C. 154(b) by 0 days.

(21) Appl. No.: 14/369,442

(22) PCT Filed: Dec. 24, 2012

(86) PCT No.: PCT/CA2012/050939
§ 371 (c)(1),
(2) Date: Jun. 27, 2014

(87) PCT Pub. No.: WO2013/097042
PCT Pub. Date: Jul. 4, 2013

(65) Prior Publication Data
US 2015/0011776 A1     Jan. 8, 2015

Related U.S. Application Data

(60) Provisional application No. 61/581,164, filed on Dec. 29, 2011.

(51) Int. Cl.
| | |
|---|---|
| *C07D 493/20* | (2006.01) |
| *C07D 307/20* | (2006.01) |
| *C07D 493/22* | (2006.01) |
| *C07D 493/04* | (2006.01) |
| *A61K 31/366* | (2006.01) |
| *C07D 405/06* | (2006.01) |
| *C07D 413/06* | (2006.01) |

(52) U.S. Cl.
CPC ............ *C07D 307/20* (2013.01); *C07D 493/22* (2013.01); *C07D 493/04* (2013.01); *A61K 31/366* (2013.01); *C07D 405/06* (2013.01); *C07D 413/06* (2013.01)

(58) Field of Classification Search
CPC ................................................... C07D 493/20
USPC ........................................ 549/264, 435, 475
See application file for complete search history.

(56) References Cited

U.S. PATENT DOCUMENTS

| | | | |
|---|---|---|---|
| 5,436,238 A | 7/1995 | Kishi et al. | |
| 6,214,865 B1 * | 4/2001 | Littlefield et al. | 514/450 |
| 2004/0192885 A1 | 9/2004 | Sharma et al. | |

FOREIGN PATENT DOCUMENTS

| | | |
|---|---|---|
| CA | 2166898 | 9/2004 |
| WO | 93/17690 | 9/1993 |
| WO | 99/65894 | 12/1999 |
| WO | 2005118565 | 12/2005 |
| WO | 2009/124237 | 10/2009 |
| WO | 2013/078559 | 6/2013 |
| WO | 2013/086634 | 6/2013 |
| WO | 2013/142999 | 10/2013 |
| WO | 2014/183211 | 11/2014 |

OTHER PUBLICATIONS

Choi et al., "Synthetic studies on the marine natural product halichondrins", Pure Appl. Chem., vol. 75, No. 1, pp. 1-17, 2003, Massachusetts (Choi_Et_Al_1).
Choi et al., "Asymmetric Ni(II)/Cr(11)-Mediated Coupling Reaction: Catalytic Process", Organic Letters, vol. 4, No. 25, pp. 4435-4438, 2002, Massachusetts (Choi_Et_Al_2).
Cook et al., "Total Synthesis of (—)-Exiguolide", Organic Letters, vol. 12, No. 4, pp. 744-747, 2010, France.
Dong et al., "New Syntheses of E7389 C14-C35 and Halichondrin C14-C38 Building Blocks: Reductive Cyclization and Oxy-Michael Cyclization Approaches", J. Am. Chem. Soc., vol. 131, pp. 15642-15646, 2009, Massachusetts.
Guo et al., "Toolbox Approach to the Search for Effective Ligands for Catalytic Asymmetric Cr-Mediated Coupling Reactions", J. Am. Chem. Soc., vol. 131, pp. 15387-15393, 2009, Massachusetts.
Han et al., "Iridium-Catalyzed anti-Diastereo- and Enantioselective Carbonyl (Trimethylsilyl)allylation from the Alcohol of Aldehyde Oxidation Level", J. Am. Chem. Soc., vol. 132, pp. 9153-9156, 2010, Texas (Han_Et_Al_1).

(Continued)

Primary Examiner — Kamal Saeed
(74) Attorney, Agent, or Firm — Grossman, Tucker, Perreault & Pfleger, PLLC

(57) ABSTRACT

Disclosed is a compound of formula 1, as shown below, where $R^1$, $R^2$, $R^3$, $R^4$, $R^5$, $R^6$ and $R^7$ are as described herein. Also, disclosed is a process for the preparation of compounds of formula 1, and intermediates used therein. The compound of formula 1 can be useful for preparation of halichondrin analogs such as Eribulin.

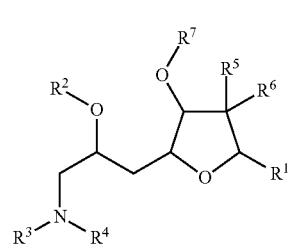

21 Claims, No Drawings

(56) References Cited

OTHER PUBLICATIONS

Han et al., Supporting Information to "Iridium-Catalyzed anti-Diastereo- and Enantioselective Carbonyl (Trimethylsilyl) allylation from the Alcohol of Aldehyde Oxidation Level", J. Am. Chem. Soc., vol. 132, pp. 9153-9156, 2010, Texas (Han_Et_Al_2).
Jackson et al., "A Total Synthesis of Norhalichondrin B", Angewandte Chemie, vol. 48, No. 13, pp. 1-132, 2009, Colorado (Jackson_Et_Al_1).
Jackson et al., "The Halichondrins and E7389", Chem. Rev., vol. 109, pp. 3044-3079, 2009, Colorado (Jackson_Et_Aa_2).
Jiang et al., "A Practical Synthesis of the F-Ring of Halichondrin B via Ozonolytic Desymmetrization of C2-Symmetric Dihydroxycyclohexene", J. Org. Chem., vol. 68, pp. 1150-1153, 2003, Wisconsin (Jiang_Et_Al_1).
Jiang et al., "A Novel Route to the F-Ring of Halichondrin B. Diastereoselection in Pd(0)-Mediated meso and C2 Diol Desymmetrization", Organic Letters, vol. 4, No. 20, pp. 3411-3414, 2002, Wisconsin (Jiang_Et_Al_2).
Kim et al., "New Syntheses of E7389 C14-C35 and Halichondrin C14-C38 Building Blocks: Double-Inversion Approach", J. Am. Chem. Soc., vol. 131, pp. 15636-15641, 2009, Massachusetts.
Kunznetsov et al., "Induction of Morphological and Biochemical Apoptosis following Prolonged Mitotic Blockage by Halichondrin B Macrocyclic Ketone Analog E7389", Cancer Research, vol. 64, pp. 5760-5766, 2004, Japan.
Litaudon et al., "Isohomoalichondrin B, a New Antitumour Polyether Macrolide from the New Zealand Deep-Water Sponge Lissodendoryx sp.", Tetrahedron Letters, vol. 35, No. 50, pp. 9435-9438, 1994, New Zealand.
Narayan et al., "Novel second generation analogs of eribulin. Part I: Compounds containing a lipophilic C32 side chain overcome P-glycoprotein susceptibility", Bioorganic & Medicinal Chemistry Letters, vol. 21, pp. 1630-1633, 2011, Massachusetts (Narayan_Et_Al_1).
Narayan et al., "Novel second generation analogs of eribulin. Part II: Orally available and active against resistant tumors in vivo", Bioorganic & Medicinal Chemistry Letters, vol. 21, pp. 1634-1638, 2011, Massachusetts (Narayan_Et_Al_2).
Narayan et al., "Novel second generation analogs of eribulin. Part III: Blood-brain barrier permeability and in vivo activity in a brain tumor model", Bioorganic & Medicinal Chemistry Letters, vol. 21, pp. 1639-1643, 2011, Massachusetts (Narayan_Et_Al_3).
Okouneva et al., "Inhibition of centromere dynamics by eribulin (E7389) during mitotic metaphase", Mol. Cancer Ther., vol. 7, No. 7, pp. 2003-2011, 2008, California.
Rudolph et al., "Early introduction of the amino group to the C27-C35 building block of Eribulin", Tetrahedron Letters, vol. 54, pp. 7059-7061, 2013, Canada.
Sabitha et al., "Synthesis of the C45-053 tetrahydropyran domain of norhalichondrins and the C14-C22 tetrahydrofuran domain of the halichondrin family", RSC Advances, vol. 2, pp. 10157-10159, 2012, India.
Sartillo-Piscil et al., "Diastereoselective synthesis of 1,2-O-isopropylidene-1,6-dioxaspiro[4,4]nonane applying the methodology of generation of radical cations under non-oxidizing conditions", Tetrahedron Letters, vol. 44, pp. 3919-3921, 2003, Mexico.
Sun et al., "Synthesis and Olefination Reactions of an a-Enal from Diacetone Glucose", Communications Synthesis, pp. 28-29, 1982, Maryland.
Trost et al., "Ru-Catalyzed Alkene-Alkyne Coupling. Total Synthesis of Amphidinolide P", J. Am. Chem. Soc., vol. 127, pp. 17921-17937, 2005, California.
Wang et al., "Structure-Activity Relationships of Halichondrin B Analogues: Modifications at C.30-C.38", Bioorganic & Medicinal Chemistry Letters, vol. 10, pp. 1029-1032, 2000, Massachusetts.
Zheng et al., "Macrocyclic ketone analogues of halichondrin B", Bioorganic & Medicinal Chemistry Letters, vol. 14, pp. 5551-5554, 2004, Massachusetts.
International Search Report and Written Opinion from corresponding PCT Appln. No. PCT/CA2012/050859, dated Jan. 29, 2013.
International Search Report and Written Opinion from related PCT Appln. No. PCT/CA2012/050939, dated Feb. 15, 2013.
International Search Report and Written Opinion from related PCT Appln. No. PCT/CA2012/050254, dated Jul. 8, 2013.
International Preliminary Report on Patentability from related PCT Appln. No. PCT/CA2012/050897, dated Jun. 17, 2014.
International Preliminary Report on Patentability from related PCT Appln. No. PCT/CA2012/050939, dated Jul. 1, 2014.
International Search Report from related PCT Appln. No. PCT/CA2014/050504, dated Jul. 24, 2014.
International Search Report and Written Opinion from related PCT Appln. No. PCT/CA2014/050438, dated Jul. 25, 2014.
Office Action from related U.S. Appl. No. 14/361,489 dated Dec. 18, 2014.

* cited by examiner

2-((2S,3S,4R,5R)-5-((S)-3-AMINO-2-HYDROXYPROP-1-YL)-4-METHOXY-3-(PHENYLSULFONYLMETHYL)TETRAHYDROFURAN-2-YL)ACETALDEHYDE DERIVATIVES AND PROCESS FOR THEIR PREPARATION

CROSS-REFERENCE TO RELATED APPLICATION

This application claims the benefit of and priority to U.S. Provisional patent application No. 61/581,164, filed Dec. 29, 2011. The content of the above-noted patent application is hereby expressly incorporated by reference into the detailed description hereof.

FIELD

The specification relates to tetrahydrofuran-2-yl acetaldehyde derivatives of formula 1, as disclosed herein, and process for their preparation.

BACKGROUND

Halinchondrin analogs have been disclosed as having anticancer and antimitotic activity (U.S. Pat. No. 6,214,865, incorporated herein by reference). In particular, Halichondrin B has been reported as a potent anticancer agent that was first isolated from the marine sponge *Halichondria okadai* (U.S. Pat. No. 6,214,865; WO 2005/118565 A1 and WO 2009/124237 A1, all incorporated herein by reference). In addition, Eribulin, a Halichondrin B analog, has been reported as having potent anticancer properties (WO 2009/124237 A1, incorporated herein by reference).

Halichondrin B

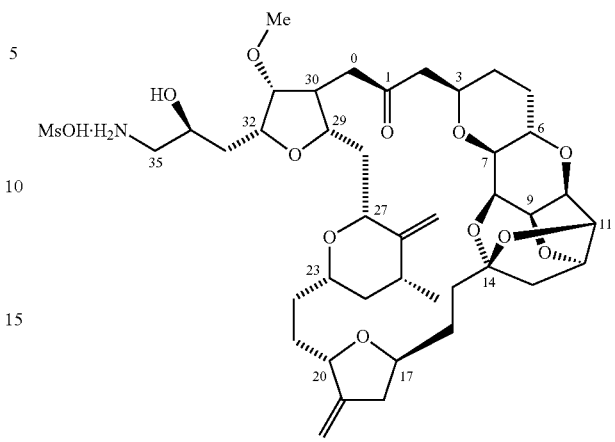

Eribulin Mesylate (where $Ms=CH_3SO_2-$)

The synthetic approach described (U.S. Pat. No. 6,214,865; WO 2009/124237 A1, *Bioorg. Med. Chem. Lett.*, 2004, 14, 5551 and *J. Am. Chem. Soc.* 2009, 131, 15642, all incorporated herein by reference) involves introduction of nitrogen in the C27-C35 fragment of Eribulin after assembly of the macrocycle. Such an approach can add synthetic steps to the later stages of the synthesis, after the building blocks corresponding to the C1-C13 and C14-C26 fragments have been introduced. The synthesis of those fragments is long and complex; and every additional step in the synthesis can imply an increase in manufacturing costs. In addition, due to the cytotoxic nature of Eribulin, late introduction of the nitrogen results in a greater number of steps that can require special safety containment, which can limit throughput and can also increase the cost of producing the active pharmaceutical ingredient (API).

There is a need in the art for a compound that corresponds to the C27-C35 fragment, and that can be used in process for preparation of Halichondrin and its analogs, including Eribu-

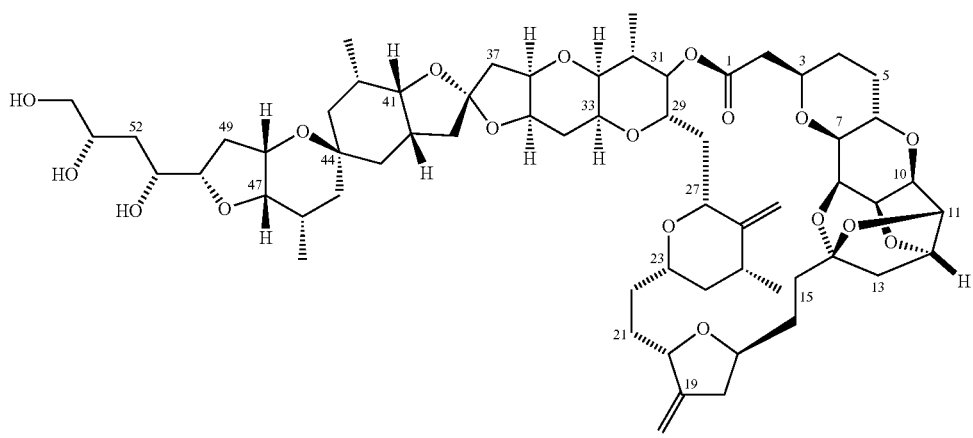

lin. In addition, there is a need in the art for a compound that can help to improve the convergence of the synthetic route for preparation of Halichondrin and its analogs, and therefore, can also help to reduce the amount of C1-C13 and C14-C26 fragments required. Further, there is a need in the art for a compound that can help to reduce the number of steps that can require safety containment for preparation of Halichondrin and its analogs. Moreover, there is a need in the art for a process for preparation of such a compound.

SUMMARY OF THE INVENTION

In one aspect, the specification discloses a compound of formula 1

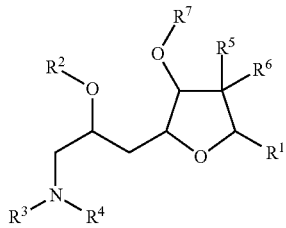

1 wherein $R^1$, $R^2$, $R^3$, $R^4$, $R^5$, $R^6$ and $R^7$ are as described herein.

In another aspect, the specification discloses a compound of formula 3

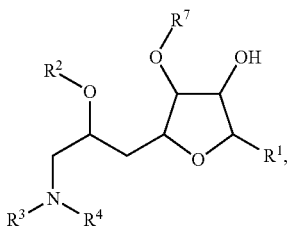

3 wherein $R^1$, $R^2$, $R^3$, $R^4$ and $R^7$ are as described herein.

In a further aspect, the specification discloses a compound of formula 4

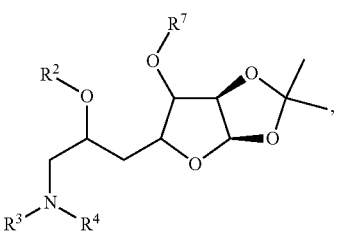

4 wherein $R^2$, $R^3$, $R^4$ and $R^7$ are as described herein.

In a still further aspect, the specification discloses processes for the preparation of the compounds of formula 1, 3 and 4.

DESCRIPTION OF EXAMPLE EMBODIMENTS

As described above, in one aspect the specification discloses a compound of formula 1

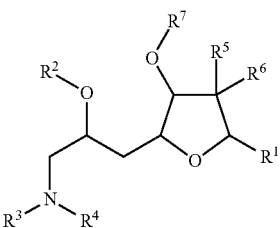

1 wherein,
$R^1$ is —CH$_2$—CH=CR$^8$R$^{8'}$, —CH$_2$—C(=O)—R$^9$ or —CH$_2$—CH$_2$—O—R$^{10}$, wherein
  $R^8$ and $R^{8'}$ each independently is H or a hydrocarbon, the hydrocarbon optionally having one or more heteroatoms;
  $R^9$ is H or OR$^{11}$, wherein $R^{11}$ is H or a hydrocarbon, the hydrocarbon optionally having one or more heteroatoms;
  $R^{10}$ is H or an alcohol protecting group;
$R^2$ is H or an alcohol protecting group;
$R^3$ and $R^4$ each independently is H, a silyl group, an acyl group, a sulfonyl group or an alkoxycarbonyl group;
  or $R^2$ and one of $R^3$ and $R^4$ together form —C(=O)—, —C(=O)—C(=O)— or —C(R$^{12}$)(R$^{13}$)—, wherein $R^{12}$ and $R^{13}$ each independently is H or a hydrocarbon, the hydrocarbon optionally having one or more heteroatoms;
$R^5$ and $R^6$ each independently is H, —CH$_2$OR$^{14}$ or —CH$_2$SO$_2$—Ar, or $R^5$ and $R^6$ taken together form =CH—SO$_2$—Ar, wherein
  $R^{14}$ is H or an alcohol protecting group; and
  Ar is an aryl group; and
$R^7$ is H, C$_{1-3}$ alkyl or C$_{1-3}$ haloalkyl.

In one embodiment, the compound has the stereochemical configuration as shown in formula 1'

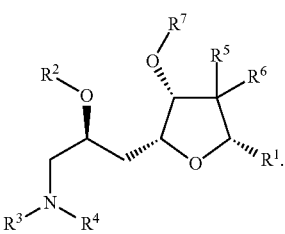

1'

The term "hydrocarbon", as used herein, refers to a group that contains hydrogen and carbon, linked generally via a carbon backbone, but may optionally include heteroatoms. Thus, groups like methyl, ethoxyethyl, 2-pyridyl, and trifluoromethyl are considered to be hydrocarbyl for the purposes of this application. Hydrocarbyl groups include, but are not limited to aryl, heteroaryl, carbocycle, heterocycle, alkyl, alkenyl, alkynyl, and combinations thereof.

The term "heteroatom" as used herein means an atom of any element other than carbon or hydrogen. Preferred heteroatoms are nitrogen, oxygen, silicon and sulfur.

The term "alcohol protecting group" as used herein is not particularly limited, and should be known to a skilled worker or can be determined (see, for example, Wuts, P. G. M.; Greene, T. W. *Greene's Protective Groups in Organic Synthesis*, 4th ed.; John Wiley & Sons, Inc.: Hoboken, N.J., 2007). In one embodiment, for example and without limitation, the protecting group forms an ester, ether or is a silyl-protecting group. In a further, embodiment for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS), tri-iso-propylsilyloxymethyl (TOM), or triisopropylsilyl (TIPS).

The term "silyl group" as used herein is not particularly limited, and should be known to a person of skill in the art. In one embodiment, for example and without limitation, the silyl group refers to the general formula "$R_3Si-$", where R is a hydrocarbon; and can include the silyl protecting groups noted above. In a further embodiment, for example and without limitation, the silyl group can optionally have one or more heteroatoms.

The term "acyl group" as used herein is not particularly limited, and should be known to a person of skill in the art. In one embodiment, for example and without limitation, the acyl group refers to the general formula "$RC(=O)-$", where R is a hydrocarbon; and can also include the acyl protecting groups noted above.

The term "sulfonyl group" as used herein is not particularly limited, and should be known to a person of skill in the art. In one embodiment, for example and without limitation, the sulfonyl group refers to the general formula "$RSO_2-$", where R is a hydrocarbon. In a further embodiment, for example and without limitation, the sulfonyl group can optionally have one or more heteroatoms.

The term "alkoxycarbonyl group" as used herein is not particularly limited, and should be known to a person of skill in the art. In one embodiment, for example and without limitation, the alkoxycarbonyl group refers to the general formula "$R-O-C(=O)-$", where R is a hydrocarbon.

The term "alkyl" as used herein is not particularly limited and should be known to a person of skill in the art; and refers to substituted or unsubstituted saturated hydrocarbon groups, including straight-chain alkyl and branched-chain alkyl groups, including haloalkyl groups such as trifluoromethyl and 2,2,2-trifluoroethyl, etc. In one embodiment, for example and without limitation, the alkyl group is a $C_{1-6}$ alkyl.

The term $C_{1-6}$alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1,2-dimethylbutyl, 1-ethyl-2-methylpropyl, 1,1,2-trimethylpropyl, 1,1-dimethylbutyl, 2,2-dimethylbutyl, 2-ethylbutyl, 1,3-dimethylbutyl, 2-methylpentyl or 3-methylpentyl.

The term "aryl" as used herein is not particularly limited, and should be known to a person of skill in the art. In one embodiment, for example and without limitation, the aryl group is a $C_{6-14}$ aryl. In another embodiment, for example and without limitation, aryl includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Examples of aryl include benzene, naphthalene, phenanthrene, phenol, aniline, anthracene, and phenanthrene.

In another aspect, the specification relates to a process for preparation of the compound of formula 1 as described above, the process containing the step of:

converting the terminal alcohol of the compound of formula 2 into an amine to form the compound of formula 1a

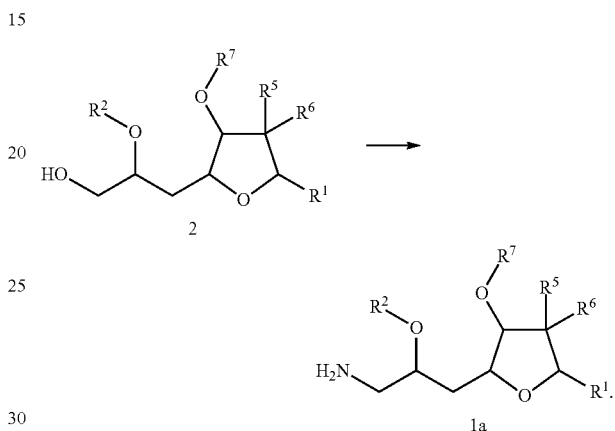

wherein $R^1$, $R^2$, $R^3$, $R^4$, $R^5$, $R^6$ and $R^7$ are as described above.

The process for conversion of the alcohol group into an amine group is not particularly limited. In one embodiment, for example and without limitation, the conversion is carried out by converting the alcohol into a leaving group to form an intermediate, followed by substitution of the leaving group by an amine or other nitrogen based nucleophile to form the compound of formula 1.

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is mesylate or tosylate.

The amine or other nitrogen based nucleophile used for formation of the amine is not particularly limited. In one embodiment, for example and without limitation, the amine used for the substitution reaction is ammonia. In another embodiment, for example and without limitation, the nitrogen based nucleophile is an azide. The azide used is also not particularly limited, and can be, in one embodiment for example, trimethylsilyl azide ($TMSN_3$).

The organic solvent used in the reactions described herein is not particularly limited and should be known to a person of skill in the art or can be determined. The particular solvent used would depend upon the reactants and the reaction being carried out, to allow the reaction to proceed. In one embodiment, for example and without limitation, the amination is carried out using ammonia, with methanol being used as a solvent.

In one embodiment, in the compound of formula 1a formed after amination and where $R^2$ is H, the hydroxyl and amine functional groups of the compound are protected. Alcohol protecting group, as described above, can be used to protect the alcohol group, and where $R^2$ is as described above.

The amine protecting group as used herein is not particularly limited and should be known to a person of skill in the art (see, for example, Wuts, P. G. M.; Greene, T. W. *Greene's Protective Groups in Organic Synthesis*, 4th ed.; John Wiley & Sons, Inc.: Hoboken, N.J., 2007). In one embodiment, for example and without limitation, amine protecting group can include carbobenzyloxy (Cbz), p-methoxybenzyloxy carbonyl (Moz), tert-butoxycarbonyl (t-BOC), 9-fluorenyl-methoxycarbonyl (FMOC), acetyl (Ac), benzoyl (Bz), carbamate, (2-trimethylsilyl)ethanesulfonyl (SES), p-methoxybenzyl (PMB), 3,4-Dimethoxybenzyl (DMPM) or p-methoxyphenyl (PMP). In a further embodiment, the amine protecting group is tert-butoxycarbonyl (t-BOC).

In one embodiment, for example, in the compound of formula 1, $R^1$ is —CH$_2$—CH═CH$_2$. In another embodiment, for example, in the compound of formula 1 $R^1$ is —CH$_2$—C(═O)H. The process for formation of the compound of formula 1 where $R^1$ is —CH$_2$—C(═O)H is not particularly limited. In one embodiment, the compound of formula 1 where $R^1$ is —CH$_2$—C(═O)H is formed from a compound where $R^1$ is —CH$_2$—CH═CH$_2$. The process for conversion is not particularly limited. In one embodiment, for example and without limitation, the conversion is carried out by oxidatively cleaving the alkene to form the aldehyde.

The process for oxidatively cleaving the alkene to an aldehyde is not particularly limited and should be known to a person of skill in the art or can be determined. In one embodiment, for example and without limitation, the oxidative cleavage is performed using osmium tetroxide/sodium periodate or by ozonolysis.

In one embodiment in the compound of formula 1, $R^5$ and $R^6$ each independently is H, —CH$_2$OR$^{14}$ or —CH$_2$SO$_2$—Ar, or $R^5$ and $R^6$ taken together form ═CH—SO$_2$—Ar, where Ar is aryl and $R^{14}$ is H or an alcohol protecting group. In a further embodiment in the compound of formula 1, one of $R^5$ and $R^6$ is —CH$_2$SO$_2$-Ph. In a still further embodiment, for example, the one of $R^5$ and $R^6$ is —CH$_2$SO$_2$-Ph and the carbon to which it is attached has the S-configuration.

The process for formation of a compound of formula 1 where $R^5$ and $R^6$ is, as described above, not particularly limited. In one embodiment, for example a compound of formula 3 is converted into the compound of formula 1, where one of $R^5$ and $R^6$ is —CH$_2$SO$_2$-Ph.

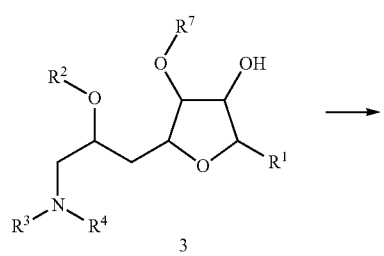

3

-continued

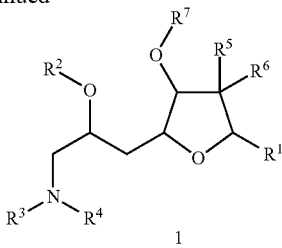

1

The process for conversion of the alcohol group into $R^5$ and $R^6$ as described above in the compound of formula 1 is not particularly limited. In one embodiment, for example and without limitation, the alcohol is oxidized to a ketone ("R'—C(═O)—R") prior to conversion to the compound of formula 1. The oxidation of the alcohol is not particularly limited, and should be known to a skilled worker or can be determined. In one embodiment, for example and without limitation, the oxidation is performed using a chromium-based reagent, such as Collins reagent, pyridinium dichromate (PDC) or pyridinium chlorochromate (PCC); activated dimethyl sulfoxide (DMSO), such as, Swern oxidation, Moffatt oxidation or Doering oxidation; or hypervalent iodine compounds, such as, Dess-Martin periodinane or 2-iodoxybenzoic acid.

Following oxidation of the alcohol to a ketone, the ketone functional group can be, in one embodiment, for example and without limitation, converted into an alkene. The reaction to convert a ketone to an alkene is not particularly limited, and should be known to a skilled worker or can be determined. In one embodiment, for example and without limitation, the ketone can be converted into an alkene using the Peterson olefination, the Wittig reaction or the like. In a further embodiment, for example and without limitation, the ketone is converted into an alkene using (EtO)$_2$POCH$_2$SO$_2$Ph.

Upon formation of the alkene, the compound can be reduced to alkane using a reducing agent. The reducing agent used in not particularly limited and can be determined by a skilled worker. In one embodiment, for example and without limitation, the reduction is carried out using a hydride source. The hydride source used is not particularly limited and should be known to a skilled worker or can be determined. In one embodiment, for example and without limitation, the hydride source is Stryker's Reagent ([(PPh$_3$)CuH]$_6$) or sodium borohydride triacetate (NaBH(OAc)$_3$).

In one embodiment in the compound of formula 1, $R^7$ is H, $C_{1-3}$ alkyl or $C_{1-3}$ haloalkyl. In a further embodiment, for example and without limitation, $R^7$ is $C_{1-3}$ alkyl. In a still further embodiment, for example and without limitation, $R^7$ is methyl.

The process for preparation of compounds of formula 1 will now be described with reference to Scheme 1 and 2, shown below.

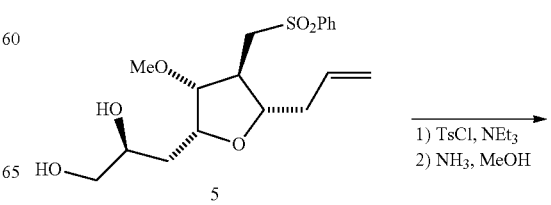

5

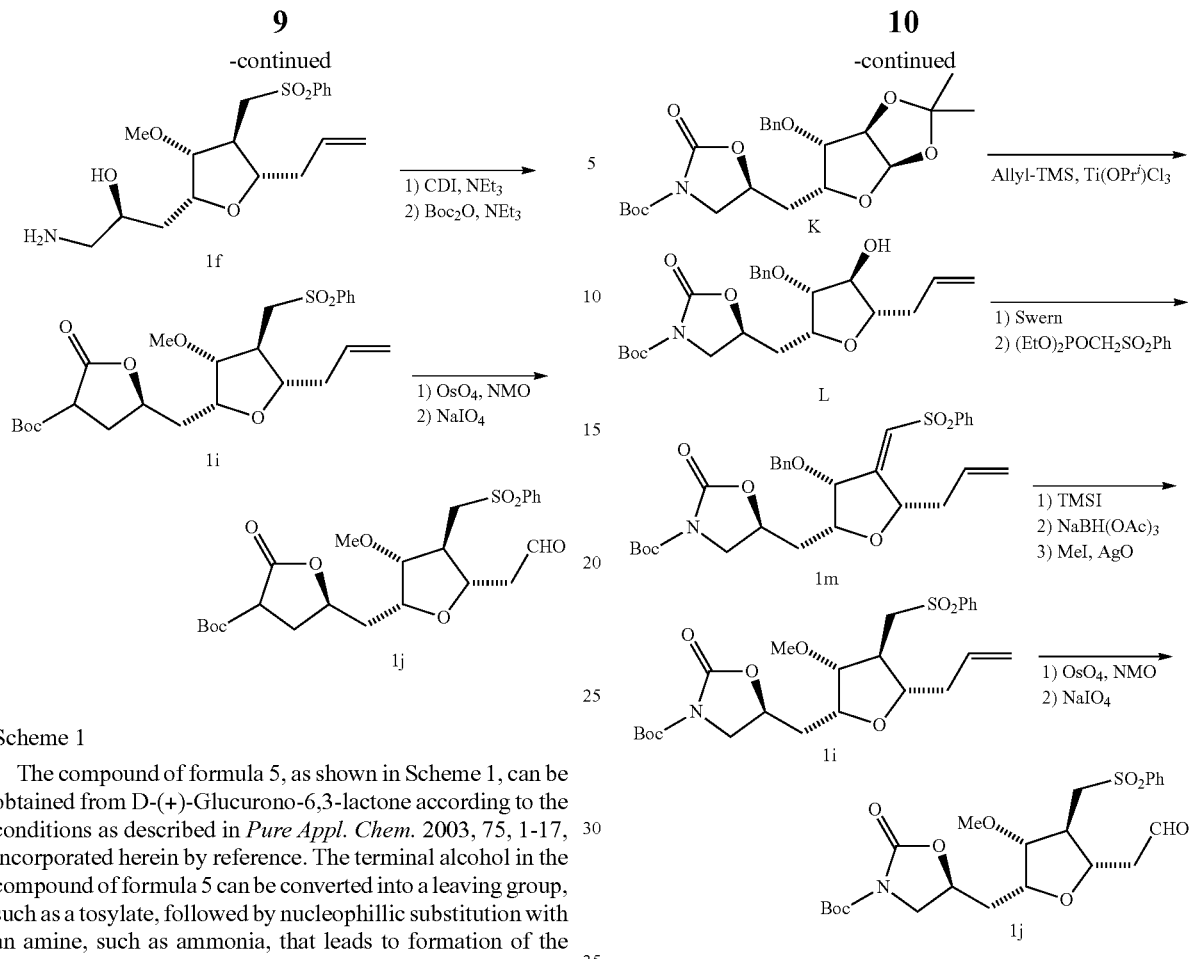

Scheme 1

The compound of formula 5, as shown in Scheme 1, can be obtained from D-(+)-Glucurono-6,3-lactone according to the conditions as described in *Pure Appl. Chem.* 2003, 75, 1-17, incorporated herein by reference. The terminal alcohol in the compound of formula 5 can be converted into a leaving group, such as a tosylate, followed by nucleophillic substitution with an amine, such as ammonia, that leads to formation of the compound of formula 1f. Reaction with 1,1'-carbonyldiimidazole (CDI) and protection of the oxazolidinone with di-tert-butyl pyrocarbonate (Boc$_2$O) leads to the compound of formula 1i. The alkene in the compound of formula 1i can then be converted to an aldehyde of formula 1j, by oxidation using osmium tetroxide and N-methyl morpholine N-oxide, followed by reaction with sodium periodate (NaIO$_4$).

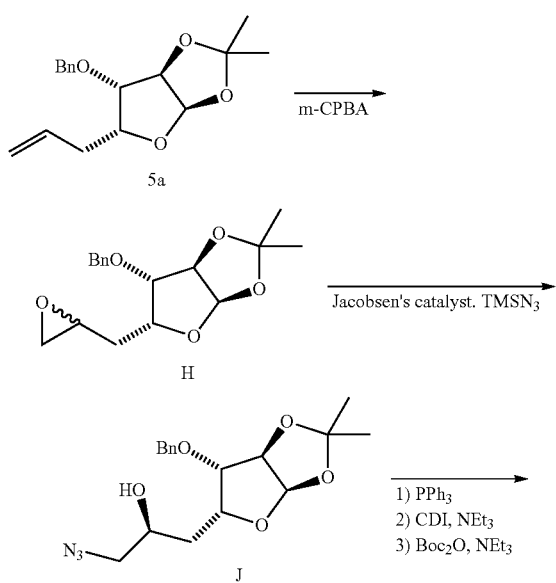

Scheme 2

Scheme 2 discloses an alternate route for the synthesis of compounds of formula 1. Formation of the epoxide of formula H can be carried out following a similar procedure as disclosed in *Org. Lett.*, 2010, 12, 744, incorporated herein by reference. Nucleophillic reaction of the compound of formula H with an azide, such as trimethylsilyl azide (TMSN$_3$) can lead to the formation of compound of formula J. The azide can be reduced using, for example and without limitation, triphenylphosphine (PPh$_3$), followed by reaction of the amine with CDI and Boc$_2$O, as described above in Scheme 1, to form the compound of formula K. Nucleophillic reaction with, for example and without limitation, allyl-trimethylsilyl in the presence of a catalyst, of the compound of formula K leads to compound of formula L.

The catalyst used for such nucleophillic reaction is not particularly limited and can be determined by a skilled worker. In one embodiment, for example and without limitation, the catalyst used is Ti(OPr$^i$)Cl$_3$.

The alcohol group in the compound of formula L can be oxidized to a ketone, followed by a Wittig or Horner-Wadsworth-Emmons type reaction to form the compound of formula 1m. The benzyl group (Bn) from the compound of formula 1m is removed using trimethylsilyl iodide (TMSI) to provide a free hydroxyl group. The arylsulfonyl alkene can be reduced using a hydride source, for example and without limitation, NaBH(OAc)$_3$. As shown in scheme 2, the reduction of the double bond by NaBH(OAc)$_3$, with a vicinal free hydroxyl group can help to direct the reduction process and to obtain the desired stereoselectivity of the arylsulfonyl alkylene. The free hydroxyl is then methylated to form the compound of formula 1i. Oxidative cleavage of the alkene functional group in the compound of formula 1i with, for example and without limitation, osmium tetroxide and N-methylmorpholine N-oxide followed by sodium periodate leads to the formation of compound 1j.

In another aspect, the specification relates to a compound of formula 3

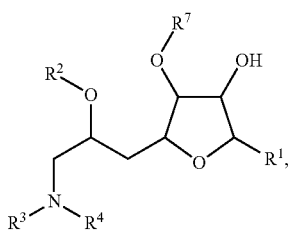

3 wherein $R^1$, $R^2$, $R^3$, $R^4$ and $R^7$ are as described herein.

In a further aspect, the specification relates to a compound of formula 4

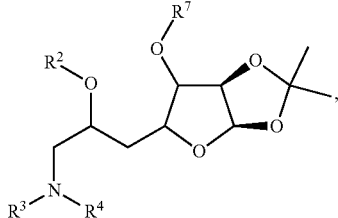

4 wherein $R^2$, $R^3$, $R^4$ and $R^7$ are as described herein.

EMBODIMENTS

1. The compound of formula 1:

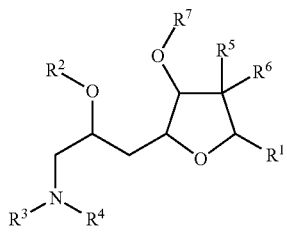

1 wherein, $R^1$ is —$CH_2$—CH=$CR^8R^{8'}$, —$CH_2$—C(=O)—$R^9$ or —$CH_2$—$CH_2$—O—$R^{10}$, wherein $R^8$ and $R^{8'}$ each independently is H or a hydrocarbon, the hydrocarbon optionally having one or more heteroatoms;

$R^9$ is H or $OR^{11}$, wherein $R^{11}$ is H or a hydrocarbon, the hydrocarbon optionally having one or more heteroatoms;

$R^{10}$ is H or an alcohol protecting group;

$R^2$ is H or an alcohol protecting group;

$R^3$ and $R^4$ each independently is H, a silyl group, an acyl group, a sulfonyl group or an alkoxycarbonyl group;

or $R^2$ and one of $R^3$ and $R^4$ together form —C(=O)—, —C(=O)—C(=O)— or —C($R^{12}$)($R^{13}$)—, wherein $R^{12}$ and $R^{13}$ each independently is H or a hydrocarbon, the hydrocarbon optionally having one or more heteroatoms;

$R^5$ and $R^6$ each independently is H, —$CH_2OR^{14}$ or —$CH_2SO_2$—Ar, or $R^5$ and $R^6$ taken together form =CH—$SO_2$—Ar, wherein $R^{14}$ is H or an alcohol protecting group; and Ar is an aryl group; and $R^7$ is H, $C_{1-3}$ alkyl or $C_{1-3}$ haloalkyl.

2. The compound according to embodiment 1, wherein the compound has the stereochemical configuration as shown in formula 1'

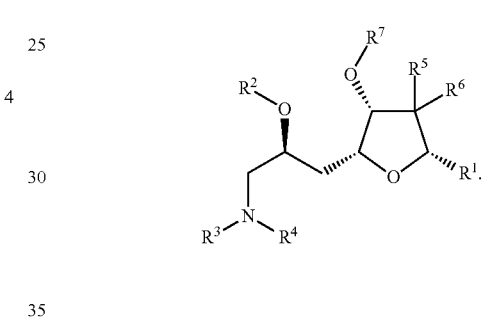

1'

3. The compound according to embodiment 1 or 2, wherein $R^1$ is —$CH_2$—CH=$CH_2$, —$CH_2$—CH=CH—$CH_3$, —$CH_2$—CH=C($CH_3$)$_2$ or —$CH_2$—C(=O)H.

4. The compound according to any one of embodiments 1 to 3, wherein $R^1$ is —$CH_2$—C(=O)H.

5. The compound according to any one of embodiments 1 to 4, wherein $R^2$ is H, a silyl group, an acyl group or an alkoxycarbonyl group.

6. The compound according to any one of embodiments 1 to 5, wherein $R^3$ and $R^4$ each independently is H, a silyl group, an acyl group, a sulfonyl group or an alkoxycarbonyl group, and at least one of $R^3$ and $R^4$ is other than H.

7. The compound according to any one of embodiments 1 to 4, wherein $R^2$ and one of $R^3$ and $R^4$ together form —C(=O)—, and other $R^3$ or $R^4$ is H, a silyl group, an acyl group, a sulfonyl group or an alkoxycarbonyl group.

8. The compound according to any one of embodiments 1 to 7, wherein one of $R^5$ and $R^6$ is H and the other is —$CH_2SO_2$—Ar.

9. The compound according to any one of embodiments 1 to 7, wherein one of $R^5$ and $R^6$ is H and the other is —$CH_2SO_2$—Ar, and the carbon to which they are attached has the S-configuration.

10. The compound according to any one of embodiments 1 to 9, wherein $R^7$ is a $C_{1-3}$ alkyl group.

11. The compound according to any one of embodiments 1 to 9, wherein $R^7$ is methyl.

12. A process for preparation of the compound of formula 1 as defined in any one of embodiments 1 to 11, the process comprising:
converting the terminal alcohol of the compound of formula 2 into an amine or substituted amine to form the compound of formula 1

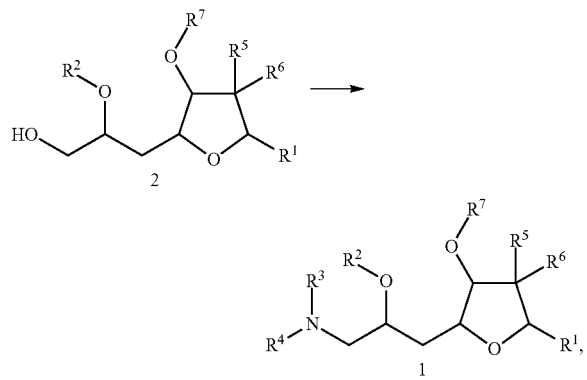

wherein $R^1$, $R^2$, $R^3$, $R^4$, $R^5$, $R^6$ and $R^7$ are as defined in embodiment 1.

13. The process according to embodiment 12, comprising converting the primary alcohol function in the compound of formula 2 into a leaving group to form an intermediate, followed by amination of the intermediate to form the compound of formula 1.

14. The process according to embodiment 13, wherein the leaving group is a sulfonate-based leaving group.

15. The process according to embodiment 14, wherein the sulfonate-based leaving group is nonaflate, triflate, fluorosulfonate, tosylate, mesylate or besylate.

16. The process according to embodiment 14, wherein the sulfonate-based leaving group is tosylate.

17. The process according to any one of embodiments 13 to 16, wherein the amination is carried out using ammonia in an organic solvent.

18. The process according to embodiment 17, wherein the organic solvent is methanol.

19. The process according to any one of embodiments 12 to 18, wherein the process involves converting the compound of formula 2 to form the compound of formula 1a 20. The process according to any one of embodiments 12 to 18, wherein $R^2$ and $R^3$ together form —C(=O)— and $R^4$ is N-tert-butoxycarbonyl (t-BOC).

21. The process according to any one of embodiments 12 to 20, wherein $R^1$ is —CH$_2$—CH=CH$_2$ (compound of formula 1b).

22. The process according to embodiment 21, further comprising oxidatively cleaving the alkene to form the aldehyde of formula 1c 23. The process according to any one of embodiments 12 to 22, wherein $R^5$ is H and $R^6$ is —CH$_2$SO$_2$Ph.

24. The process according to any one of embodiments 12 to 23, wherein $R^7$ is methyl.

25. A process for preparation of the compound of formula 1 as defined in any one of embodiments 1 to 11, the process comprising:
converting the alcohol group of the compound of formula 3 to form the compound of formula 1

26. The process according to embodiment 25, wherein the alcohol is oxidized to a ketone prior to conversion to the compound of formula 1.

27. The process according to embodiment 26, wherein the oxidation is carried out using Swern oxidation.

28. The process according to embodiment 26 or 27, wherein a Wittig or a Horner-Wadsworth Emmons reaction is carried out on the ketone to form the compound of formula 1.

29. The process according to embodiment 28, wherein the ketone is reacted with $(EtO)_2POCH_2SO_2Ph$ to form a compound of formula 1d

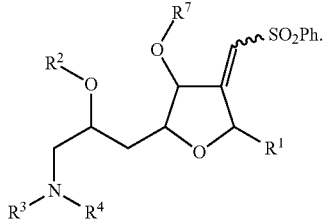

1d

30. The process according to embodiment 29, wherein the alkene is reduced to form the compound of formula 1e

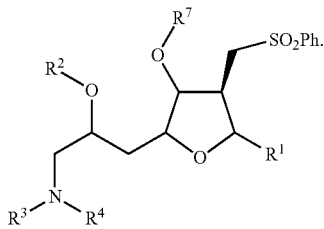

1e

31. The process according to embodiment 30, wherein the reduction is carried out using a hydride source.

32. The process according to embodiment 31, wherein the hydride source is $NaBH(OAc)_3$.

33. The process according to any one of embodiments 25 to 32, wherein $R^1$ is $-CH_2-CH=CH_2$.

34. The process according to embodiment 33, further comprising oxidatively cleaving the alkene to form the aldehyde.

35. The process according to any one of embodiments 25 to 34, wherein $R^2$ and $R^3$ form $-C(=O)-$ and $R^4$ is N-tert-butoxycarbonyl (t-BOC).

36. The process according to any one of embodiments 25 to 34, wherein $R^2$ and $R^3$ form $-C(R^{12})(R^{13})-$, wherein $R^{12}$ and $R^{13}$ each independently is H or a hydrocarbon, the hydrocarbon optionally having one or more heteroatoms.

37. The process according to any one of embodiments 25 to 36, wherein $R^7$ is methyl.

38. The process according to any one of embodiments 25 to 37, wherein the compound of formula 3 is formed by converting a compound of formula 4 into the compound of formula 3

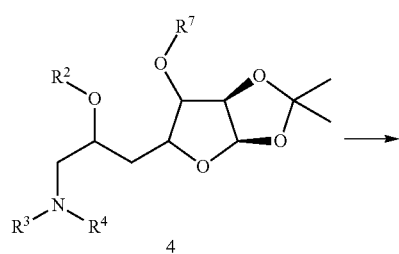

4

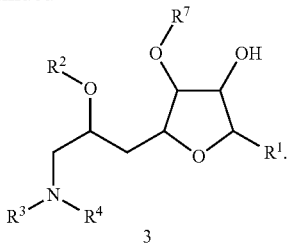

3

39. The process according to embodiment 38, wherein the conversion to form the compound of formula 3 is carried out using nucleophilic addition of an allyl silane.

40. The process according to embodiment 39, wherein the nucleophilic addition is carried out using allyl-TMS in the presence of a catalyst, whereby TMS stands for trimethylsilyl.

41. The process according to embodiment 40, wherein the catalyst is $Ti(OPr^i)Cl_3$.

42. The process according to any one of embodiments 37 to 41, wherein the compound of formula 4 is formed by conversion of a compound of formula 5 to form the compound of formula 4

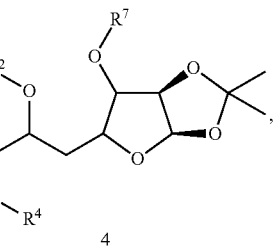

5

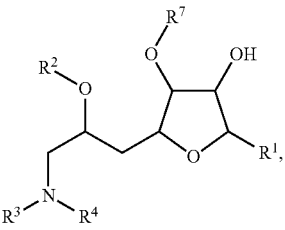

4 wherein $R^2$, $R^3$, $R^4$ and $R^7$ are as defined in embodiment 1.

43. The process according to embodiment 42, wherein the conversion is carried out by nucleophilic addition of an amine or an azide.

44. The process according to embodiment 43, wherein the intermediate formed upon addition of the azide is reduced to form the compound of formula 4.

45. The compound of formula 3

3 wherein $R^1$, $R^2$, $R^3$, $R^4$ and $R^7$ are as defined in embodiment 1.

46. A process for preparation of the compound of formula 3, comprising the process as defined in any one of embodiments 37 to 40.

47. The compound of formula 4

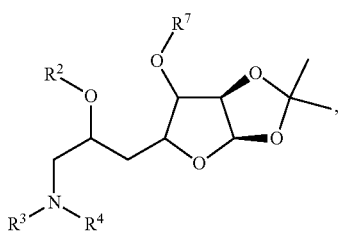

wherein $R^2$, $R^3$, $R^4$ and $R^7$ are as defined in embodiment 1.

48. A process for preparation of the compound of formula 4, comprising the process as defined in any one of embodiments 42 to 44.

49. A process for preparation of a halichondrin analog, comprising the process as defined in any one of embodiments 12-44.

50. A process for preparation of Eribulin, comprising the process as defined in any one of embodiments 12-44.

EXAMPLES

The invention is now described by way of examples, which disclose embodiments of the inventions, and are not intended to be limiting of the invention as described and set herein.

Example 1

Preparation of Compound of Formula 5a

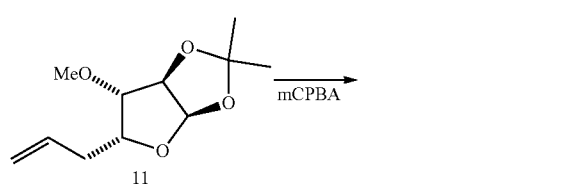

Epoxide of formula 5a was prepared by oxidation of compound of formula 11 with m-Chloroperbenzoic acid (mCPBA), following the procedure described in Org. Lett. 2010, 12, 744.

Example 2

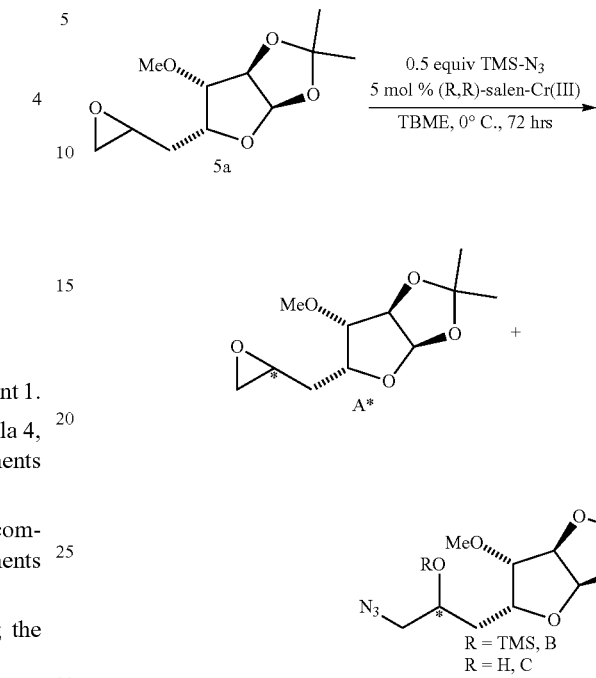

A dry reaction vessel equipped with a stir bar and rubber septum, under an atmosphere of $N_2$, was charged with compound 5a (1 wt. parts). Compound 5a was dissolved in anhydrous methyl t-butyl ether (MTBE, 1.6 vol. parts) and the resulting solution was cooled to 0° C. (R,R)-salen-Cr(III) (0.01 eq, 0.03 wt. parts) and trimethylsilyl azide (TMSN$_3$) (0.50 eq, 0.25 wt. parts) were added to the solution of 5a at 0° C. and the resulting reaction mixture was stirred at 0° C. for 72 hrs. The volatiles were removed under reduced pressure and the crude mixture was separated by column chromatography (stationary phase: SiO$_2$, eluent: 1:0-7:13 heptanes:EtOAc) to afford single isomers A* (0.49 eq.) and B+C (0.49 eq.) as colourless oils.

Example 3

Preparation of Compound of Formula 2a

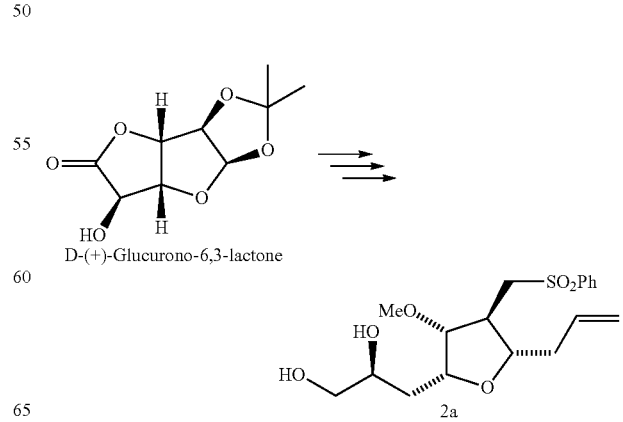

The diol of formula 2a was prepared from D-(+)-Glucurono-6,3-lactone according to the conditions described in *Pure Appl. Chem.* 2003, 75, 1-17.

Example 4

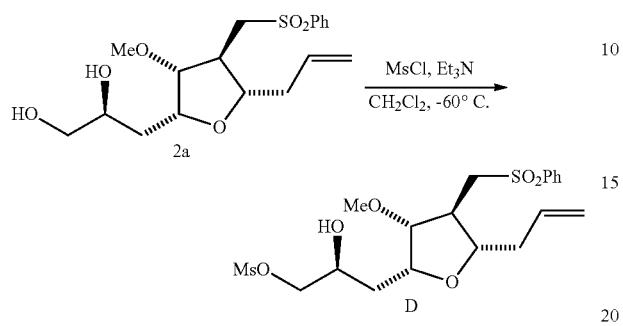

Compound 2a (1 wt. parts) is dissolved in CH$_2$Cl$_2$ (14 vol. parts) and the resulting solution is cooled to an internal temperature of −60° C. Triethylamine (Et$_3$N) (1.1 eq., 0.3 wt. parts) and methanesulfonyl chloride (MsCl) (1.1 eq., 0.3 wt. parts) are added sequentially at −60° C. The internal temperature of the reaction mixture is kept below −52° C. The reaction is run at −60° C. for 45 min, until no further conversion is detected by thin layer chromatography (TLC) (1:1 heptanes:EtOAc). The reaction is quenched with water (5 vol. parts), warmed to room temperature and the organic layer is separated. The aqueous layer is further extracted with CH$_2$Cl$_2$ (2×5 vol. parts) and the combined organic layers are dried over Na$_2$SO$_4$, filtered and concentrated in vacuo. The crude mixture is purified by column chromatography (stationary phase: SiO$_2$, 1:0-1:1 heptanes:EtOAc) to afford compound of formula D.

Example 5

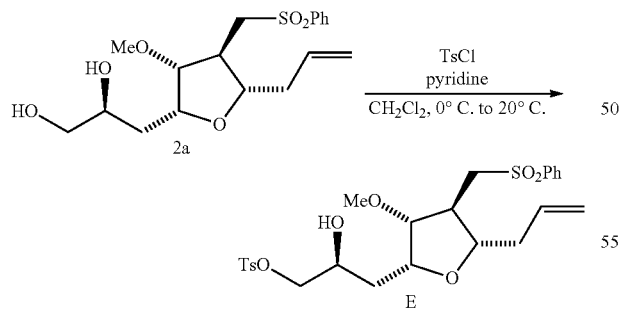

Compound 2a (1 wt. parts) is dissolved in CH$_2$Cl$_2$ (5.7 vol. parts) and the resulting solution is cooled to 0° C. To the solution of 2a is added pyridine (5.0 eq., 1.1 wt. parts), catalytic 4-dimethylaminopyridine (DMAP) and 4-toluenesulfonyl chloride (TsCl) at 0° C. The reaction mixture is allowed to slowly warm to room temperature and is stirred at room temperature until TLC analysis (eluent: 1:1 heptanes:EtOAc) indicates the reaction to be complete. The reaction is quenched with sat. aq. NH$_4$Cl (5 vol. parts). The organic layer is separated and washed once more with sat. aq. NH$_4$Cl, followed by 1M aq. HCl. The organic layer is dried over Na$_2$SO$_4$, filtered and concentrated in vacuo. The crude product is purified by column chromatography (stationary phase: SiO$_2$, eluent: 3:1-1:1 heptanes:EtOAc) to obtain E.

Example 6

Preparation of Compound of Formula 1e

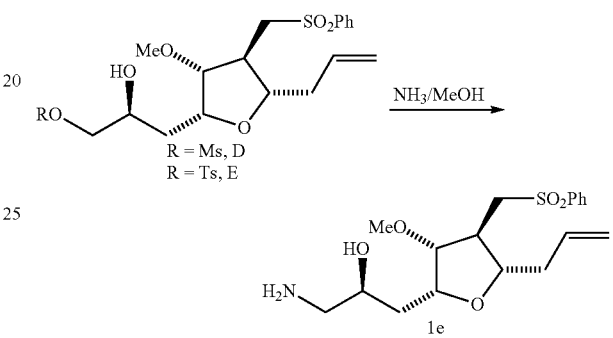

Compound D or E (1 wt. parts). is dissolved in 7 N NH$_3$ in methanol (33 vol. parts) and stirred at room temperature for 3 days, or until TLC analysis (eluent: 1:1 heptanes:EtOAc) indicates that the starting material is consumed. The volatiles are removed under reduced pressure and the crude mixture is redissolved in CH$_2$Cl$_2$ and washed with sat. aqueous NaHCO$_3$. The organic layer is separated, dried over Na$_2$SO$_4$, filtered and concentrated under reduced pressure to afford crude 1e which is used without further purification.

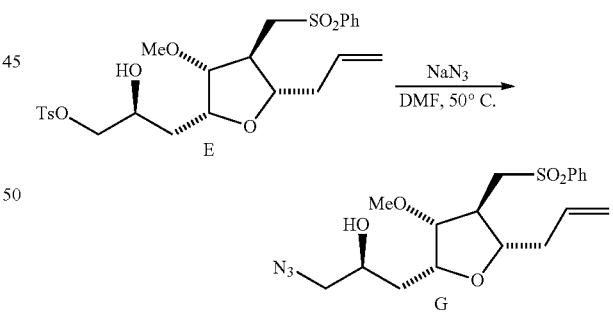

Compound E (1 wt. parts) is dissolved in dimethylformamide (DMF) (20 vol. parts) and to this solution is added NaN$_3$ (6.5 eq. 0.82 wt. parts) at room temperature. The reaction mixture is heated to 50° C. until TLC analysis (eluent: 1:1 heptanes:EtOAc) indicates the starting material to be consumed. The reaction mixture is quenched with water, diluted with diethyl ether and the layers are separated. The aqueous layer is further extracted with diethyl ether and the combined organics are dried over Na$_2$SO$_4$, filtered and concentrated reduced pressure. The crude product G is used without further purification.

Example 8

Preparation of the Compound of Formula 1f

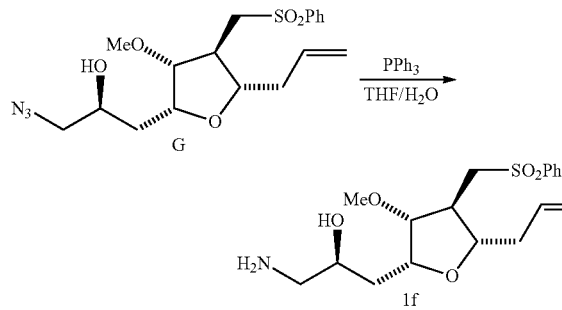

Crude product G (1 wt. parts) is dissolved in tetrahydrofuran (THF) (10 vol. parts) and to this solution is added triphenylphosphine (PPh$_3$) (1.1 eq. 0.58 wt. parts) and water (1 vol. parts). The reaction mixture is stirred at room temperature until TLC analysis (eluent: 1:1 heptanes:EtOAc) indicates that the starting material has been consumed. The reaction is quenched with water and diluted with ethyl acetate (EtOAc). The layers are separated and the aq. layer is extracted twice more with EtOAc. The combined organics are dried over Na$_2$SO$_4$, filtered and concentrated to afford crude 1f, which is used without purification.

Example 9

Preparation of Compound of Formula 1g

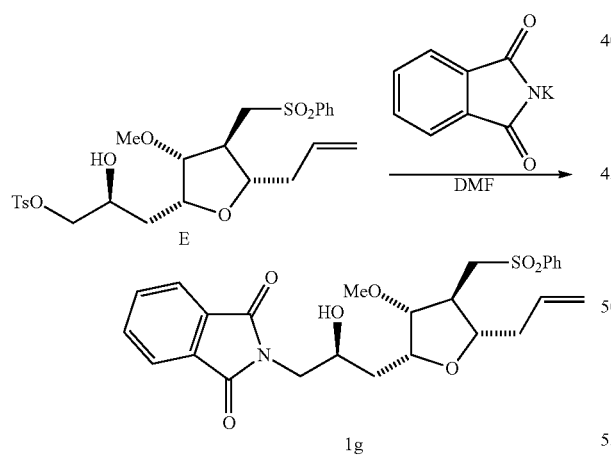

Compound E (1 wt. parts) is dissolved in dimethylformamide (DMF) (20 vol. parts) and to this solution is added potassium phthalimide (3.0 eq. 1.1 wt. parts) at room temperature. The reaction mixture is stirred at room temperature until TLC analysis (eluent: 1:1 heptanes:EtOAc) indicates that the starting material is consumed. The reaction mixture is quenched with water, diluted with diethyl ether and the layers are separated. The aqueous layer is further extracted with diethyl ether and the combined organics are dried over Na$_2$SO$_4$, filtered and concentrated under reduced pressure. The crude product is purified by column chromatography (stationary phase: SiO$_2$, eluent: 1:0-1:1 heptanes:EtOAc) to afford 1g.

Example 10

Preparation of Compound of Formula 1h

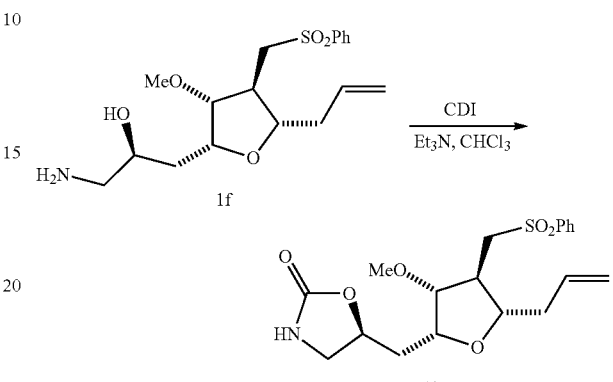

Compound 1f (1 wt.) is dissolved in CHCl$_3$ (11 vol. parts) and to the resulting solution triethylamine (Et$_3$N) (1.5 eq., 0.42 wt. parts) and 1,1'-carbonyldiimidazole (CDI) (1.5 eq., 0.33 wt. parts) are added. The reaction mixture is stirred at room temperature until TLC analysis (eluent: 95:5 CH$_2$Cl$_2$:MeOH) shows that the starting material has been consumed. The reaction mixture is diluted with CH$_2$Cl$_2$ and washed twice with water and once with brine. The organic layer is dried over Na$_2$SO$_4$, filtered and concentrated. The crude product is purified by column chromatography (stationary phase: SiO$_2$, eluent: 9:1-6:4 CH$_2$Cl$_2$:acetone) to afford 1h.

Example 11

Preparation of Compound of Formula 1i

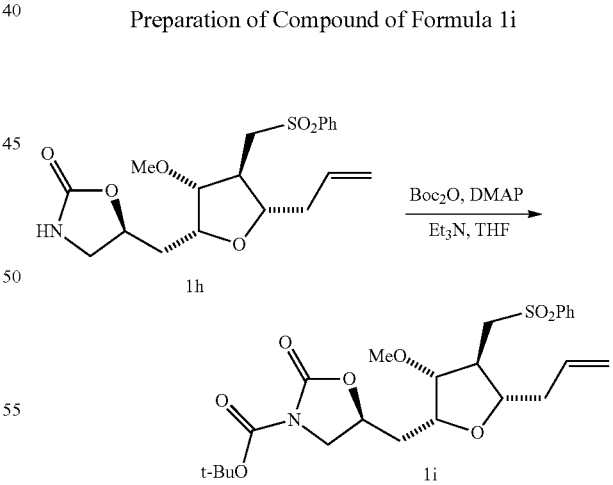

Compound 1h (1 wt. parts) is dissolved in tetrahydrofuran (THF) (71 vol. pars) and to this solution are added triethylamine (Et$_3$N) (1.2 eq, 0.29 wt. parts), catalytic 4-dimethylaminopyridine (DMAP) and di-tert-butyl pyrocarbonate (Boc$_2$O) (1.3 eq., 0.71 wt. parts) at room temperature. The reaction is stirred at room temperature until TLC analysis (eluent: 8:2 CH$_2$Cl$_2$:acetone) shows that the starting material has been consumed. The reaction mixture is diluted with ethyl acetate (EtOAc) and washed sequentially with water and 1M aqueous HCl. The organic layer is dried over Na$_2$SO$_4$, filtered and concentrated to afford crude 1i, which is used without further purification.

Example 12

Preparation of Compound 1j

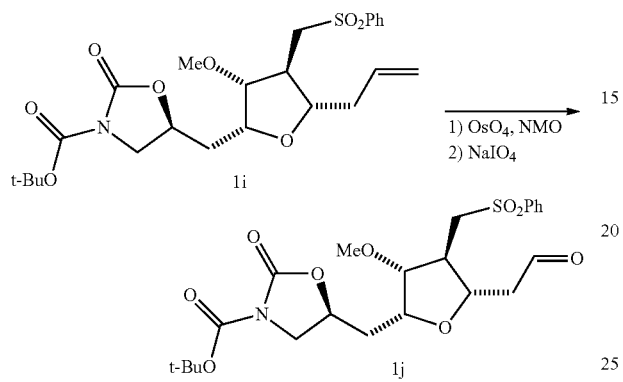

To a solution of alkene 1i (1.28 mmol) in CH$_2$Cl$_2$ (8 mL) at room temperature is added 4-methylmorpholine N-oxide (NMO) (3.84 mmol, 3.0 equiv) and a solution of OSO$_4$ (0.10M in H$_2$O, 0.020 equiv). The resulting mixture is vigorously stirred for 1.5 h and 0.5M aqueous solution of sodium bisulfite (10 mL) is then added. After stirring for 30 min at room temperature, the mixture is extracted with CH$_2$Cl$_2$ (10 mL×3) and the combined organic layers are washed with brine (10 mL), dried over MgSO$_4$, filtered and concentrated under vacuum. The resulting residue is dissolved in CH$_2$Cl$_2$ (10 mL) and a saturated NaHCO$_3$ aqueous solution (0.25 mL) is added, followed by slow addition of NaIO$_4$ (3.84 mmol, 3.0 equiv) with vigorous stirring. After stirring for 5 h at room temperature, the reaction mixture is filtered and the resulting filtrate is concentrated under reduced pressure to give crude compound 1j.

Example 13

Preparation of Compound of Formula 1k

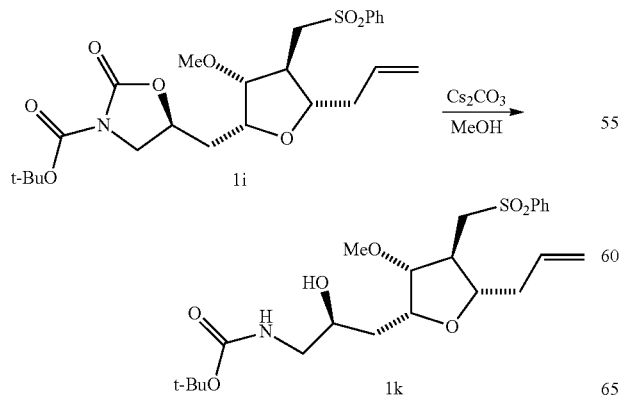

Compound 1i (1 wt. parts) is dissolved in methanol (MeOH) (32 vol. parts) and to this solution is added Cs$_2$CO$_3$ (0.2 eq, 0.13 wt. parts) at room temperature. The reaction is stirred at room temperature until TLC analysis (eluent: 8:2 CH$_2$Cl$_2$:acetone) shows that the starting material has been consumed. The reaction mixture is partitioned between water and ethyl acetate (EtOAc) and the organic layer is separated. The aqueous layer is extracted twice more with EtOAc and the combined organics are dried over Na$_2$SO$_4$, filtered and concentrated under reduced pressure to afford 1k.

Example 14

Preparation of Compound of Formula 1m

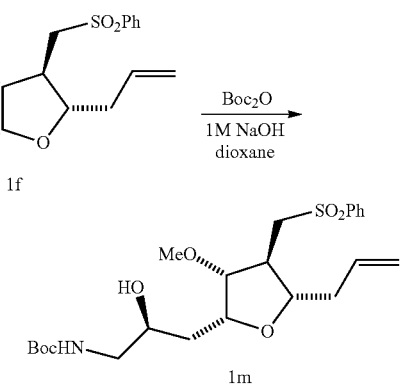

To a solution of 1f (2.3 g, 6.3 mmol, 1.0 eq) in 1M aqueous NaOH (30 mL) and dioxane (30 mL) at room temperature was added a solution of di-tert-butyl dicarbonate (1.6 g, 7.5 mmol, 1.2 eq.) in 1,4-dioxane (30 mL), in one portion. The reaction mixture was stirred at room temperature for 16 hours. TLC showed that the reaction was complete. The reaction was quenched with 1M aqueous HCl until the pH of the reaction mixture reached 6-7. The total volume of the reaction mixture was reduced by half under vacuum and subsequently partitioned between ethyl acetate (100 mL) and additional water (100 mL). The layers were separated and the aqueous layer was further extracted with ethyl acetate (2×100 mL) and the combined organic layers were washed with brine (100 mL), dried over MgSO$_4$ and concentrated to a light yellow oil. The crude 1m was used in the subsequent step without any further purification.

Example 15

Preparation of Compound of Formula 1n

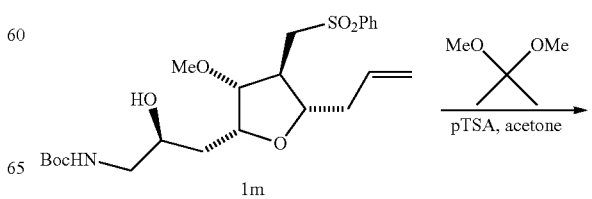

-continued

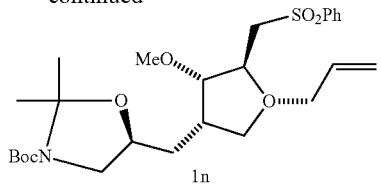

To a solution of crude 1m (6.3 mmol, 1.0 eq.) in acetone (100 mL) was added 2,2-dimethoxypropane (7.7 mL, 63 mmol, 10 eq.) in one portion, followed by p-toluenesulfonic acid (69 mg, 0.6 mmol, 0.1 eq.) at room temperature. The reaction mixture was stirred at room temperature for 16 hrs. TLC showed that the reaction was complete. The reaction was quenched with triethylamine (0.1 mL, 0.7 mmol, 0.11 eq) and the volatiles were removed under reduced pressure. The crude material was dissolved in dichloromethane and purified by column chromatography on silica gel using a gradient 5-10% acetone in dichloromethane as eluent to afford 1n (79% over two steps) as a sticky colorless oil.

Example 16

Preparation of Compound of Formula 1o

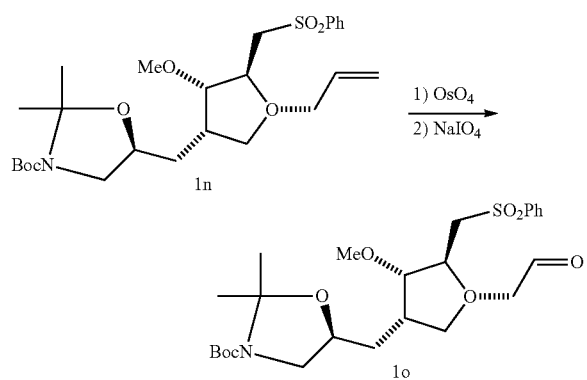

To a solution of 1n (5.5 g, 10.8 mmol, 1.0 eq.) in dichloromethane (60 mL) was added 4-methylmorpholine-N-oxide (3.8 g, 32.4 mmol, 3.0 eq) at room temperature, followed by a solution of OsO$_4$ (2.5% (w/w) in t-BuOH, 1.4 mL, 0.11 mmol, 0.01 eq), dropwise. The reaction mixture was stirred for 2.5 hours and quenched with 10% (w/w) aqueous solution of Na$_2$S$_2$O$_3$ (100 mL). The resulting mixture was stirred for 15 minutes and the layers were separated. The aqueous layer was extracted with additional dichloromethane (2×50 mL) and the combined organics were dried over MgSO$_4$, filtered and concentrated to afford a diol intermediate, which was used in the subsequent step without any further purification.

In a separate 250 mL round-bottom flask, NaIO$_4$ (6.9 g, 32 mmol, 3.0 eq) was suspended in dichloromethane (20 mL) and saturated aqueous sodium bicarbonate solution (3 mL) was added. The diol intermediate (from the previous step) was dissolved in dichloromethane (40 mL) and added to the reaction mixture at room temperature. The reaction mixture was stirred for 16 hours. The reaction solution was decanted from the reaction vessel, washed with saturated aqueous sodium bicarbonate solution (50 mL), brine (50 mL) and dried over MgSO$_4$, filtered and concentrated. The product was purified by column chromatography on silica gel using a gradient 5-10% acetone in dichloromethane as eluent, to afford the product 1o as a sticky colourless oil (83% over 2 steps).

Example 17

Preparation of Compound of Formula 1p

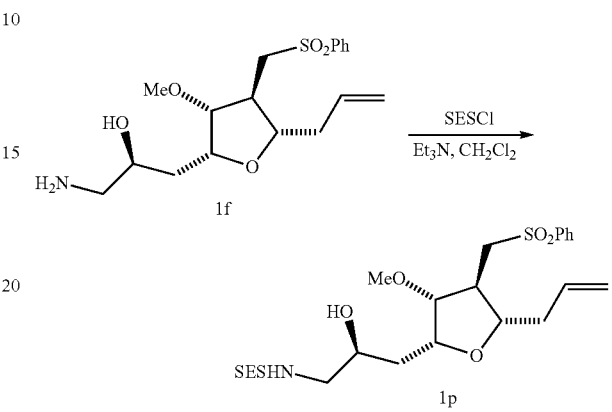

To a solution of the amino alcohol (100 mg, 0.27 mmol, 1.0 eq) in anhydrous dichloromethane (3 mL) at 0° C. was added triethylamine (75 µL, 0.54 mmol, 2.0 eq.) and 2-(trimethylsilyl)ethanesulfonyl chloride (SESCl, 0.1 mL, 0.53 mmol, 1.95 eq.) in one portion. The reaction mixture was stirred at 0° C. for 15 min before the ice bath was removed. The reaction mixture was then warmed to rt (20° C.) and stirred for 3 hours. TLC showed that the reaction was complete. The reaction was quenched with saturated aqueous ammonium chloride solution (10 mL), further diluted with dichloromethane (10 mL) and the layers separated. The aqueous layer was further extracted with dichloromethane (2×10 mL) and the combined organic layers were washed with brine (10 mL), dried over MgSO$_4$ and concentrated. The crude product was purified by column chromatography on silica gel using a gradient 10-20% acetone in dichloromethane as eluent to afford the SES-protected amino alcohol 1p (53%) as a sticky colourless oil.

Example 18

Preparation of Compound of Formula 1q

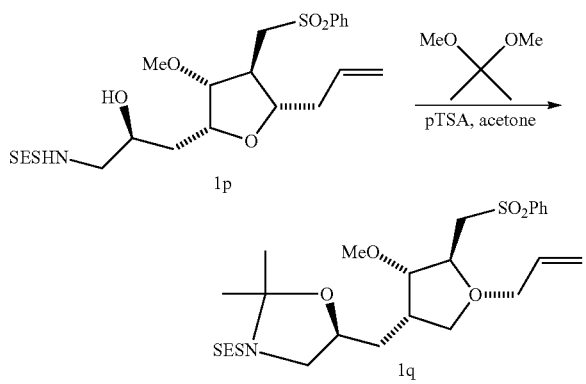

To a solution of the SES-protected amino alcohol 1p (75 mg, 0.14 mmol, 1.0 eq.) in acetone (2.5 mL) was added 2,2-dimethoxypropane (0.17 mL, 1.4 mmol, 10 eq.) in one portion, followed by p-toluenesulfonic acid (3 mg, 0.01 mmol, 0.1 eq.) at room temperature. The reaction mixture was stirred at room temperature for 16 hrs. The reaction was quenched with saturated aqueous sodium bicarbonate solution (10 mL) and further diluted with methyl t-butyl ether (MTBE) (10 mL). The layers were separated and the aqueous layer was further extracted with MTBE (2×10 mL). The combined organic layers were dried over MgSO$_4$, filtered and concentrated. The crude material was dissolved in dichloromethane and purified by column chromatography on silica gel using a gradient 5-10% acetone in dichloromethane as eluent to afford SES-acetonide protected amino alcohol 1q (46%) as a colorless oil.

Example 19

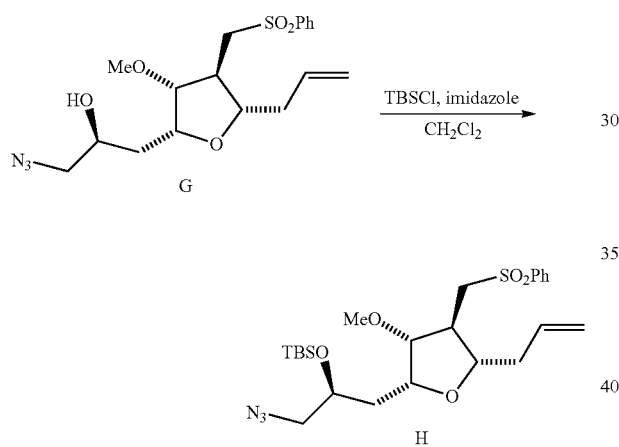

To a solution of the crude azido alcohol G (0.19 mmol, 1.0 eq.) in anhydrous dichloromethane (2 mL) were added imidazole (16 mg, 0.23 mmol, 1.2 eq.), tert-butyldimethylsilyl chloride (TBS-Cl) (34 mg, 0.23 mmol, 1.2 eq.) and a catalytic amount of DMAP at room temperature. The reaction mixture was stirred at room temperature for 16 hrs. The reaction was quenched with water (10 mL) and further diluted with dichloromethane (10 mL). The layers were separated and the aqueous layer was further extracted with dichloromethane (2×10 mL). The combined organic layers were washed with brine (10 mL), dried over MgSO$_4$, filtered and concentrated. The crude material was purified by column chromatography on silica gel using a gradient 0-50% ethyl acetate in heptane as eluent to afford the TBS-protected azido alcohol H (47%) (where TBS is tert-butyldimethylsilyl) as a colourless oil.

Certain adaptations and modifications of the described embodiments can be made. Therefore, the above discussed embodiments are considered to be illustrative and not restrictive.

What is claimed is:

1. The compound of formula 1:

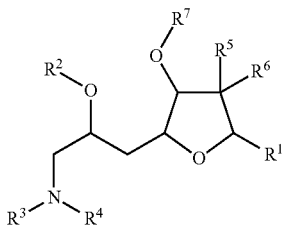

wherein,

R$^1$ is —CH$_2$—CH=CR$^8$R$^{8'}$, —CH$_2$—C(=O)—R$^9$ or —CH$_2$—CH$_2$—O—R$^{10}$, wherein R$^8$ and R$^{8'}$ each independently is H or a hydrocarbon, the hydrocarbon optionally having one or more heteroatoms;

R$^9$ is H or OR$^{11}$, wherein R$^{11}$ is H or a hydrocarbon, the hydrocarbon optionally having one or more heteroatoms;

R$^{10}$ is H or an alcohol protecting group;

R$^2$ is H or an alcohol protecting group;

R$^3$ and R$^4$ each independently is H, a silyl group, an acyl group, a sulfonyl group or an alkoxycarbonyl group;

or R$^2$ and one of R$^3$ and R$^4$ together form —C(=O)—, —C(=O)—C(=O)— or —C(R$^{12}$)(R$^{13}$)—, wherein R$^{12}$ and R$^{13}$ each independently is H or a hydrocarbon, the hydrocarbon optionally having one or more heteroatoms;

R$^5$ and R$^6$ each independently is H, —CH$_2$OR$^{14}$ or —CH$_2$SO$_2$—Ar, or R$^5$ and R$^6$ taken together form =CH—SO$_2$—Ar, wherein R$^{14}$ is H or an alcohol protecting group; and Ar is an aryl group; and R$^7$ is H, C$_{1-3}$ alkyl or C$_{1-3}$ haloalkyl.

2. The compound according to claim 1, wherein the compound has the stereochemical configuration as shown in formula 1'

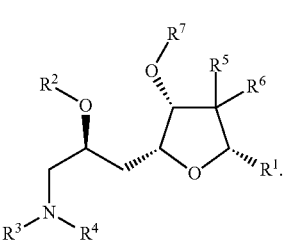

3. The compound according to claim 2, wherein R$^1$ is —CH$_2$—CH=CH$_2$, —CH$_2$—CH=CH—CH$_3$, —CH$_2$—CH=C(CH$_3$)$_2$ or —CH$_2$—C(=O)H.

4. The compound according to claim 1, wherein one of R$^5$ and R$^6$ is H and the other is —CH$_2$SO$_2$—Ar.

5. The compound according to claim 1, wherein R$^7$ is methyl.

6. A process for preparation of the compound of formula 1 as defined in claim 1, the process comprising:

converting the terminal alcohol of the compound of formula 2 into an amine or substituted amine to form the compound of formula 1

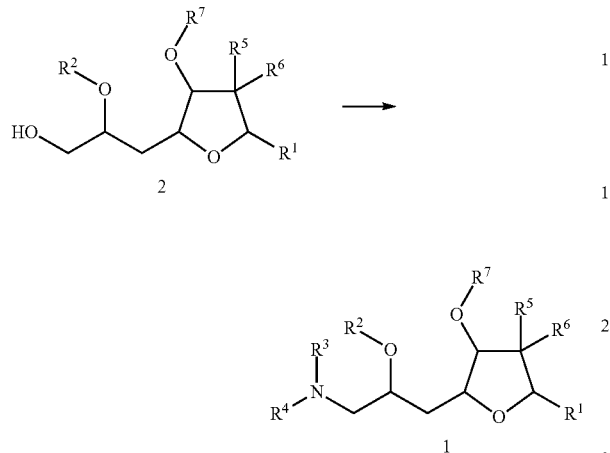

wherein $R^1$, $R^2$, $R^3$, $R^4$, $R^5$, $R^6$ and $R^7$ are as defined in claim 1.

7. The process according to claim 6, comprising converting the primary alcohol function in the compound of formula 2 into a leaving group to form an intermediate, followed by amination of the intermediate to form the compound of formula 1.

8. The process according to claim 6, wherein $R^1$ is —CH$_2$—CH═CH$_2$ (compound of formula 1b).

9. The process according to claim 8, further comprising oxidatively cleaving the alkene to form the aldehyde of formula 1c

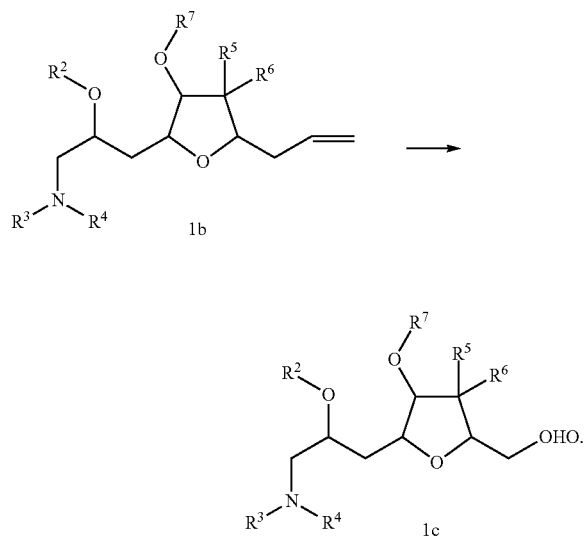

10. The process according to any one of claim 6, wherein $R^5$ is H and $R^6$ is —CH$_2$SO$_2$Ar.

11. The process according to claim 6, wherein $R^7$ is methyl.

12. A process for preparation of the compound of formula 1 as defined in claim 1, the process comprising:

converting the alcohol group of the compound of formula 3 to form the compound of formula 1

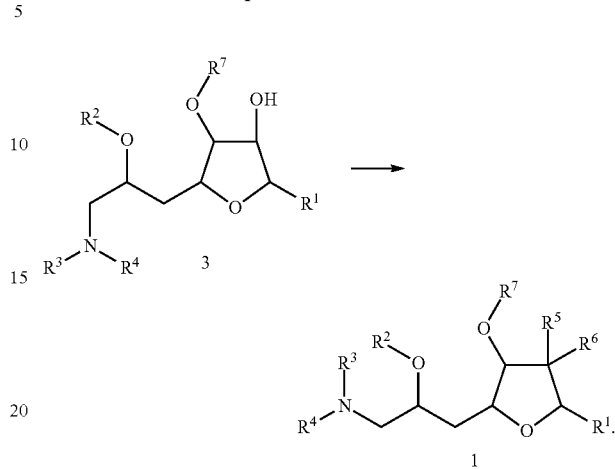

13. The process according to claim 12, wherein the alcohol is oxidized to a ketone prior to conversion to the compound of formula 1.

14. The process according to claim 12, wherein the compound of formula 3 is formed by converting a compound of formula 4 into the compound of formula 3

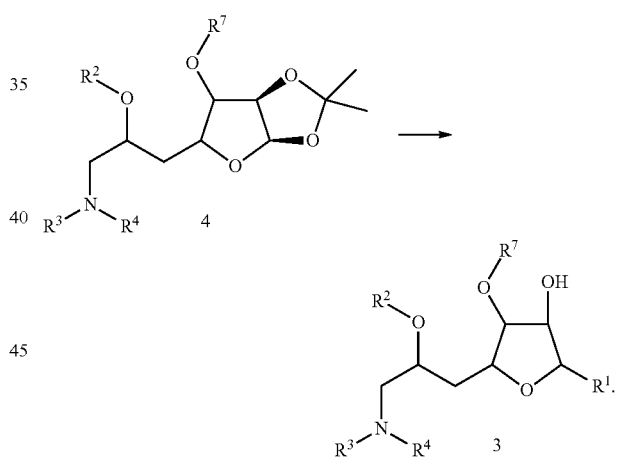

15. The process according to claim 14, wherein the conversion to form the compound of formula 3 is carried out using nucleophilic addition of an allyl silane.

16. The process according to claim 14, wherein the compound of formula 4 is formed by conversion of a compound of formula 5 to form the compound of formula 4

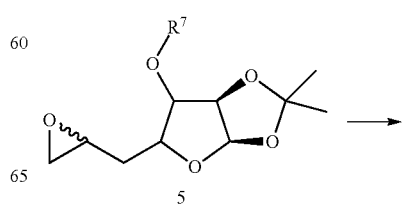

-continued

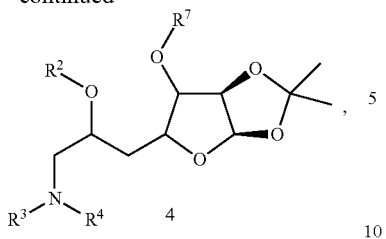

, 5 wherein $R^2$, $R^3$, $R^4$ and $R^7$ are as defined in claim 1.

17. The compound of formula 3

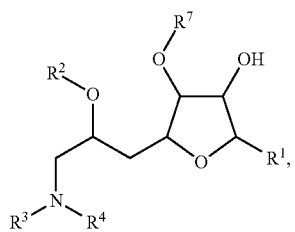

, 3 wherein $R^1$, $R^2$, $R^3$, $R^4$ and $R^7$ are as defined in claim 1.

18. A process for preparation of the compound of formula 3, comprising the process as defined in claim 14.

19. The compound of formula 4

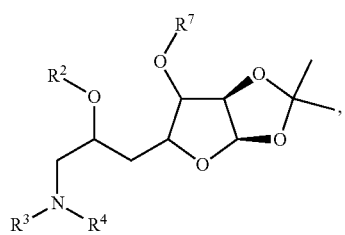

, 4 wherein $R^2$, $R^3$, $R^4$ and $R^7$ are as defined in claim 1.

20. A process for preparation of the compound of formula 4, comprising the process as defined in claim 16.

21. A process for preparation of a halichondrin analog, comprising the process as defined in claim 6.

* * * * *